United States Patent [19]
Snell et al.

[11] Patent Number: 5,759,199
[45] Date of Patent: Jun. 2, 1998

[54] SYSTEM AND METHOD FOR AMBULATORY MONITORING AND PROGRAMMING OF AN IMPLANTABLE MEDICAL DEVICE

[75] Inventors: Jeffery D. Snell, Oak Park; Jeffrey D. Konopka, Northridge, both of Calif.

[73] Assignee: Pacesetter, Inc., Sylmar, Calif.

[21] Appl. No.: 510,449

[22] Filed: Aug. 2, 1995

[51] Int. Cl.⁶ .................................................. A61N 1/36
[52] U.S. Cl. ........................ 607/60; 607/32; 607/59; 128/903
[58] Field of Search ........................ 607/32, 60, 59; 128/903

[56] References Cited

U.S. PATENT DOCUMENTS

| | | | |
|---|---|---|---|
| 4,223,679 | 9/1980 | Schulman et al. | 607/32 |
| 4,809,697 | 3/1989 | Causey, III et al. | 128/903 |
| 5,113,869 | 5/1992 | Nappholz et al. | 128/903 |
| 5,329,625 | 7/1994 | Kannan et al. | 395/275 |
| 5,336,245 | 8/1994 | Adams et al. | 607/32 |
| 5,342,408 | 8/1994 | deCoriolis et al. | 607/32 |
| 5,383,915 | 1/1995 | Adams | 607/60 |
| 5,411,536 | 5/1995 | Armstrong | 607/60 |
| 5,416,695 | 5/1995 | Stutman et al. | 364/413.02 |
| 5,626,630 | 5/1997 | Markowitz et al. | 607/32 |

FOREIGN PATENT DOCUMENTS

| | | | |
|---|---|---|---|
| 8602567 | 5/1986 | WIPO | 607/59 |

*Primary Examiner*—William E. Kamm
*Assistant Examiner*—Carl H. Layno

[57] ABSTRACT

A system and method for ambulatory monitoring and programming of an implantable medical device are provided. The system enables ambulatory communication between a modified programmer/analyzer and an implantable medical device having telemetric communication capability. This is accomplished through the use of an ambulatory interface unit which may be conveniently attached to the patient's body using a belt or harness. The ambulatory interface unit wirelessly communicates with both the programmer/analyzer and the implantable medical device thereby providing for improved patient mobility. The ambulatory interface unit may include an integral telemetry head or may be connected to the telemetry head by a communication cable.

37 Claims, 4 Drawing Sheets

SYSTEM AND METHOD FOR AMBULATORY MONITORING AND PROGRAMMING OF AN IMPLANTABLE MEDICAL DEVICE

BACKGROUND OF THE INVENTION

The present invention relates to monitoring and programming systems for use with implantable medical devices including implantable cardiac pacemakers, implantable cardiac defibrillators, as well as implantable cardioverters and combination cardioverter/defibrillators. More particularly, this invention relates to specific improvements to such systems that facilitate ambulatory monitoring and programming of implantable medical devices.

The use of implantable medical devices for diagnosing and treating of a variety of medical conditions has gained wide acceptance over the recent past. One broad category of implantable medical devices known as "implantable cardiac stimulating devices" includes devices which detect potentially malignant cardiac arrhythmias and administer therapeutic electrical stimulation in response to detected arrhythmias.

Implantable cardiac stimulating devices are commonly categorized by the type of cardiac arrhythmia they are intended to detect and treat. For example, "pacemakers" are frequently implanted in patients who suffer from bradycardia—a condition characterized by an abnormally slow heart rate. Pacing pulses administered by a cardiac pacemaker cause the patient's heart to expand and contract at a physiologically acceptable rate, thereby preventing symptoms commonly associated with bradycardia, such as dizziness, headaches, shortness of breath, and fainting. Some modern pacemakers (commonly known as "demand pacemakers") are able to sense the patient's intrinsic heart rate, and deliver pacing pulses only when the intrinsic heart rate falls below a "threshold rate." The threshold rate is typically a programmable parameter that is set by a physician in accordance with the physiological requirements of the patient.

Some pacemakers (commonly known as "rate-responsive pacemakers") also include the ability to vary the patient's heart rate in accordance with the level of physical exertion being experienced by the patient. When the patient performs activities demanding physical exertion, the pacemaker gradually increases the maintained heart rate as the amount of exertion increases, until a maximum heart rate is reached. As the amount of physical exertion decreases, the pacemaker correspondingly decreases the maintained heart rate until the threshold rate is reached. Thus, rate-responsive pacemakers advantageously permit bradycardia patients to engage in physical activities that may otherwise be harmful.

Other types of implantable cardiac stimulating devices are used to detect and treat tachycardia and fibrillation. In tachycardia, the patient's heart continues to rhythmically expand and contract, but it does so at a greater than normal rate. This adversely affects the hemodynamic performance of the heart because it has less of an opportunity to fill with blood between beats. When a patient experiences an episode of fibrillation, the cardiac tissue quivers chaotically. Because the chaotic quivering of the cardiac tissue renders the heart ineffective as a pump, fibrillation is the most severe cardiac arrythmia.

Some modern implantable devices that are intended to interrupt arrhythmias such as tachycardia and fibrillation do so by employing a "tiered therapy" approach. These devices determine an appropriate form of therapeutic electrical stimulation to be administered to the heart in accordance with the severity of the detected arrhythmia. Generally, the aggressiveness of the delivered therapy increases as the severity of an arrhythmia increases or as less aggressive therapies fail. For example, some devices may respond to an occurrence of tachycardia by first administering antitachycardia pacing pulses. Antitachycardia pacing pulses are similar to bradycardia pacing pulses, but they are administered in specific sequences that are known to be successful at interrupting tachycardia. However, should antitachycardia pacing pulses prove to be unsuccessful, the device may resort to administering a higher energy shock (typically within the range of about 2 joules to about 5 joules) known as a cardioversion shock. If the arrhythmia deteriorates into fibrillation, the device may deliver a still higher energy shock (typically within the range of about 10 joules to about 40 joules) known as a defibrillation shock. In addition, some devices which are intended to treat tachycardia and fibrillation are also able to provide bradycardia pacing therapy.

Implantable cardiac stimulating devices must be able to acquire and analyze sensory data pertaining to the patient's medical condition in order to properly administer therapies such as those described above. One of the more common sources of information is the patient's intracardiac electrogram (IEGM). Implantable medical devices typically sense a patient's IEGM through leads that are also used to administer electrical stimulation therapy. Modern implantable cardiac stimulating devices can also acquire information from other sources in order to improve the way in which pathological medical conditions are treated. For example, some devices may acquire and use information pertaining to the mechanical activity of the patient's heart, as described in commonly-assigned, copending U.S. Pat. application Ser. No. 08/091,636, filed Jul. 14, 1993, of Causey and Moberg, entitled "IMPLANTABLE LEADS INCORPORATING CARDIAC WALL ACCELERATION SENSORS AND METHOD OF FABRICATION." As another illustration, rate-responsive pacemakers typically receive and use sensory information representative of the patient's activity level in order to adjust the pacing rate, as described in commonly-assigned U.S. Pat. No. 5,383,473, granted Jan. 24, 1995 to Moberg, entitled "RATE-RESPONSIVE IMPLANTABLE STIMULATION DEVICE HAVING A MINIATURE HYBRID-MOUNTABLE ACCELEROMETER-BASED SENSOR AND METHOD OF FABRICATION," which patent is hereby incorporated herein by reference.

When a medical device is implanted in a patient, the physician typically performs a procedure during which a plurality of programmable parameters are set in accordance with the medical condition of the patient. The implantable medical device may be programmed immediately after the surgical procedure, and if necessary, during subsequent follow-up visits (during which the performance of the implantable medical device is evaluated by the physician). Examples of programmable parameters in the pacemaker context include threshold rate (described above), pacing pulse amplitude, and pacing pulse width. Of course, the programmable parameters vary greatly depending upon the type of implantable medical device being programmed.

The programming of implantable medical devices is typically accomplished through the use of a programmer/analyzer which telemetrically communicates with the implantable medical device. The implantable medical device may transmit various types of information to the programmer/analyzer. That information may include, for example, sensory data used by the implantable medical device during the delivery of therapy (e.g., the IEGM, the cardiac wall motion data, and the physical activity data described above) and operational parameters of the implantable cardiac stimulating device (e.g., battery voltage, battery impedance, and lead integrity data). Additionally, the implantable cardiac stimulating device may transmit information relating to the status of its programmable parameters and any data representative of the occurrence of physiological events and the responses of the implantable medical device to those events. After reviewing the information received from the implantable medical device, the physician can use the programmer/analyzer to reprogram the implantable medical device if the data indicates that reprogramming is desirable.

Telemetric communication with the implantable medical device is normally accomplished through the use of a telemetry head that is connected to the programmer/analyzer by a cable which is usually about 6 feet in length. The telemetry head serves as an antenna for transmitting and receiving radio frequency signals. These signals convey the information described above (e.g., sensory data, marker data, reprogrammed parameters, and commands) as well as other information from the implantable cardiac device to the programmer/analyzer. Unfortunately, the distance within which communications can be established between the telemetry head and the implantable medical device is limited to a few inches (usually no more than about 3 to 6 inches).

To accommodate the limited range of communication, the telemetry head is typically placed on the patient's body in the immediate vicinity of the implantable medical device. For example, to communicate with a pacemaker, the telemetry head is usually placed adjacent the pacemaker while the patient is lying in a face-up position. Unfortunately, this arrangement severely restricts the mobility of the patient, since any bodily motion could cause the telemetry head to fall off. Thus, the patient must usually remain in an essentially fixed position until the communication session is ended. Alternatively, an adhesive tape can be used to secure the telemetry head to the patient's body. However, this approach also restricts the patient's mobility because the patient is tethered by the cable to the programmer/analyzer, which is often not easily moveable. The range of motion available to the patient is limited by the length of the cable. Even if the physician chose to move the programmer/analyzer along with the patient, the patient mobility's would still be encumbered by the connecting cable, and the physician's mobility would be limited by the programmer's power cord.

Presently, the physician does not have the benefit of evaluating the performance of the implantable medical device while the patient is ambulatory. For example, a physician may wish to determine if a rate-responsive pacemaker properly increases the patient's heart rate as the patient performs physical activities requiring varying levels of exertion. In order to evaluate the pacemaker as the patient undergoes a modest amount of exertion, it may be desirable for the patient to simply walk back and forth across a room of the medical care facility. However, real-time monitoring of data collected by the pacemaker as the patient performs even this simple exercise could be difficult, because, as explained above, the patient's activities would be limited by the communication cable tethering the patient to the relatively immobile programmer/analyzer. Even stationary exercises such as those performed on treadmills or exercise bicycles could prove burdensome, because it may be difficult to keep the telemetry cable clear of the patient or the exercise equipment as the patient performs the physical activity. This and other difficulties associated with limited patient mobility have yet to be adequately addressed.

SUMMARY OF THE INVENTION

The present invention provides an ambulatory monitoring and programming system for implantable medical devices. The ambulatory monitoring and programming system of the present invention overcomes the difficulties associated with the use of known systems of communication between implantable medical devices and programmer/analyzers.

The ambulatory monitoring and programming system of the present invention overcomes these difficulties by extending the patient's range of mobility by employing wireless communication between a programmer/analyzer and an ambulatory interface unit. As stated, conventional monitoring systems have a telemetry head connected to a programmer/analyzer by a communication cable, and since the telemetry head is secured to the patient the cable restricts patient mobility to an area corresponding to the length of the communication cable.

This invention provides an ambulatory interface unit which eliminates the need for a physical connection between the telemetry head and the programmer/analyzer. The ambulatory interface unit may be combined with the telemetry head into one self-contained unit or, alternatively, may be connected by a short cable to the telemetry head and secured to the patient. Both embodiments allow for greatly increased patient mobility.

The ambulatory interface unit is preferably a small, battery-powered device that may be conveniently secured to the patient with, for example, a shoulder harness or belt. The ambulatory interface unit serves as an intermediary device for facilitating wireless communication between a modified programmer/analyzer and the implantable medical device. Both the ambulatory interface unit and the modified programmer/analyzer include circuitry which enable each device to transmit and receive wireless transmissions. Preferably, the wireless transmissions are radio frequency signals and both devices are set to transmit and receive on a fixed frequency. The method of modulation may be either amplitude or frequency modulation.

Since there is no tissue between the modified programmer/analyzer and the externally worn ambulatory interface unit, and since power availability is not a critical concern for externally worn devices (because the batteries are easily replaceable), the range of wireless communication between the modified programmer/analyzer and the ambulatory interface unit greatly exceeds the range of telemetric communication between conventional programmer/analyzers and implantable medical devices.

The ambulatory interface unit preferably includes an integral telemetry head which communicates with the implantable medical device in a manner that is analogous to conventional telemetric communication between implantable medical devices and programmer/analyzers. The integrated ambulatory interface unit may be secured anywhere on a patient's body limited only by the transmission range of the implanted device.

Alternatively, the telemetry head may be coupled to the ambulatory interface unit by a telemetry cable. However, because the ambulatory interface unit is preferably secured to the patient, the telemetry cable can be much shorter and kept close to the body, so as to significantly reduce any encumbering effect that the telemetry cable may have on patient mobility. For example, the ambulatory interface unit may be clipped on to a patient's belt and connected to a telemetry head (that is secured to the patient's chest in the vicinity of the implanted device) by a short cable. While still affording the patient increased mobility, this embodiment allows a larger unit to be carried by the patient which can accommodate a longer-life battery and greater range capabilities. Since communication between the ambulatory interface unit and the modified programmer/analyzer is wireless, the patient's mobility is not restricted by a physical connection to the programmer/analyzer.

The communication cable connecting the telemetry head to the ambulatory interface unit is necessitated because the telemetry head must be within approximately six inches from older implanted devices. However, as implantable devices mature, their range of communication will inevitably increase. Thus, the present invention includes within its scope a combined ambulatory interface unit and telemetry head device that can be, for example, clipped onto a patient's belt without the need to position a device in the immediate vicinity (3-6 inches) of the implantable device.

In a preferred embodiment of the present invention, patient mobility is further improved through the use of a tablet computer-based programmer/analyzer. A particularly preferred programmer/analyzer which may be modified for use with the ambulatory interface unit of the present invention is described in commonly-assigned, copending U.S. Pat. application Ser. No. 08/510,367, filed concurrently herewith, of Snell and Levin, entitled "IMPROVED USER INTERFACE FOR AN IMPLANTABLE MEDICAL DEVICE USING AN INTEGRATED DIGITIZER DISPLAY SCREEN," which is hereby incorporated by reference in its entirety. That patent application discloses a programmer/analyzer implemented on a convenient handheld tablet computer that offers sophisticated programming and analytical tools for use with implantable medical devices. A physician using the tablet computer-based programmer/analyzer is able to carry the programmer/analyzer much like a notebook. Information received from the implantable medical device may be displayed on an integrated digitizer display screen. The information so displayed can be manipulated on the digitizer display screen by the use of a pen-shaped input device which provides input to the digitizer display screen. Further, the physician can reprogram the implantable medical device by entering the appropriate information to the digitizer display screen through use of the pen-shaped input device.

To more fully exploit its potential advantages, the tablet computer-based programmer/analyzer is modified in accordance with the principles of the present invention to communicate with the above-described ambulatory interface unit. This arrangement combines the advantages of improved patient mobility (through the use of the ambulatory interface unit) with improved physician mobility (through the use of the tablet computer-based programmer/analyzer), thereby providing the opportunity for completely unencumbered ambulatory monitoring of the patient.

The combination of the ambulatory interface unit and the modified tablet computer-based programmer/analyzer allows the physician to monitor the patient and the implantable medical device while the patient performs physical activities which otherwise would be extremely difficult or impossible. For example, the physician can evaluate the performance of a rate-responsive pacemaker while the patient walks along the hallways or grounds of the medical care facility. Alternatively, the physician can escort the patient to an exercise equipment room, and monitor the pacemaker while patient performs exercises on equipment that may not be available in the vicinity of conventional monitoring equipment.

The present invention also includes a method for communicating between the implantable medical device and the programmer/analyzer. The method employs wireless communication between the programmer/analyzer and the implanted medical device. The method uses wireless communications to allow increased patient mobility. Patient mobility can be further increased by the use of the tablet computer-based programmer/analyzer to communicate with the ambulatory interface unit.

Of course, many advantages of the present invention could be achieved by modifying a programmer/analyzer other than a tablet computer-based programmer/analyzer to communicate with the ambulatory interface unit. In addition, a device which merely displays or monitors information transmitted from the implantable medical device could be advantageously modified to communicate with the ambulatory interface unit, if so desired.

BRIEF DESCRIPTION OF THE DRAWINGS

The above and other objects and advantages of the invention will be apparent upon consideration of the following detailed description, taken in conjunction with the accompanying drawings, in which like reference characters refer to like parts throughout, and in which.

DETAILED DESCRIPTION OF THE PREFERRED EMBODIMENT

Figure 1:
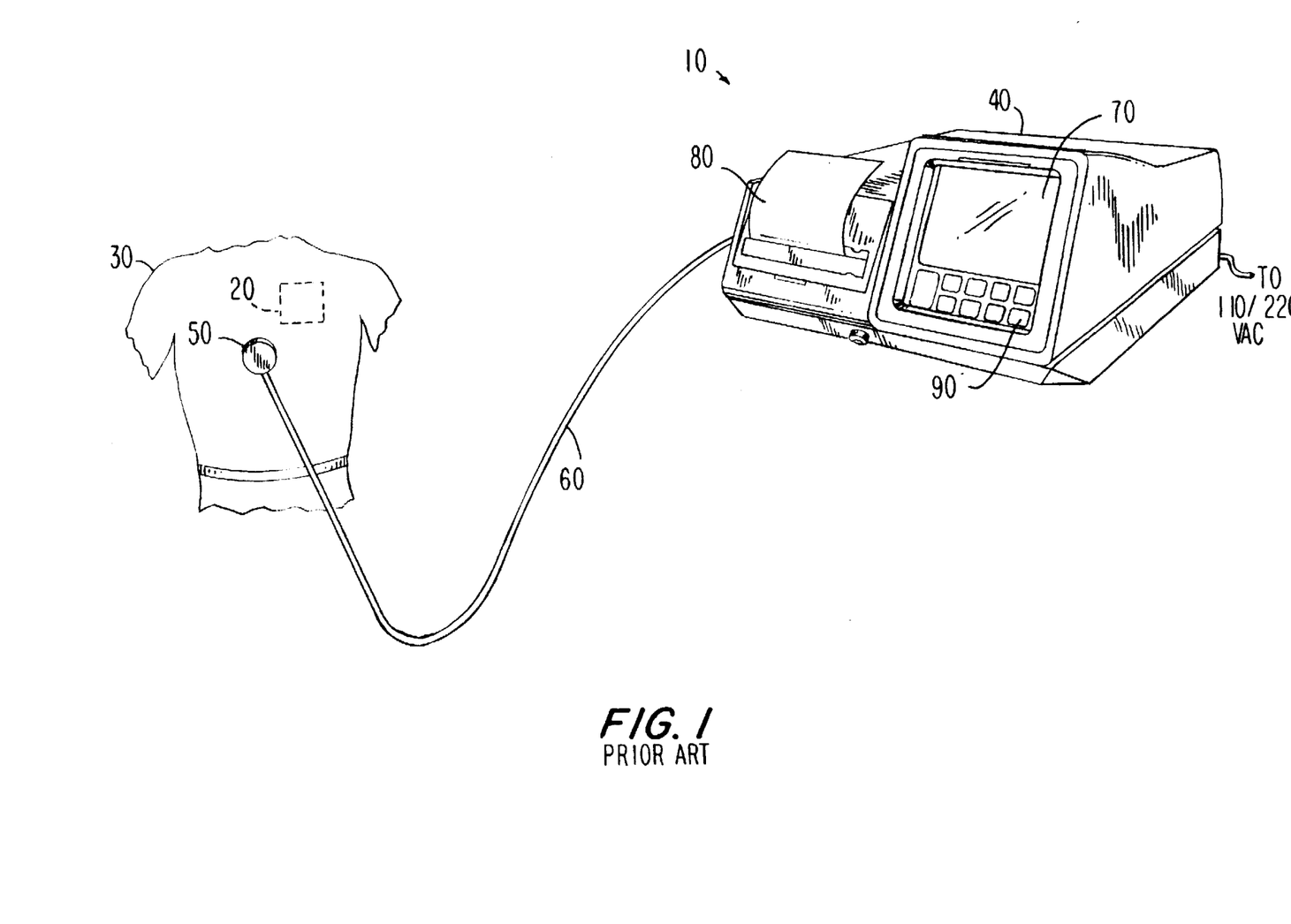
FIG. 1 depicts a conventional monitoring and programming system in which a programmer/analyzer communicates with an implantable medical device using a conventional telemetry head and cable.

FIG. 1 shows a conventional programming and monitoring system 10 for use with a medical device 20 implanted in a patient 30. The conventional programming and monitoring system 10 includes a conventional programmer/analyzer 40 and a telemetry head 50. The programmer/analyzer 40 is connected to the telemetry head 50 by a communication cable 60. In typical operation, the telemetry head 50 receives data from the implantable device 20 and transmits the data through the cable 60 to the programmer/analyzer 40. Data is displayed to a physician by either a touch screen display monitor 70 or a hardcopy printout 80.

Transmission of information to the implantable device 20 is accomplished by first entering data into the programmer/analyzer 40. Entering of data may be accomplished through the touch screen display monitor 70, a keypad 90, or a data transfer device such as, for example, magnetic disk drives (not shown). The programmer/analyzer 40 then transmits the entered data through the communication cable 60 to the telemetry head 50 which, in turn, transmits the data to the implantable device 20 by conventional telemetry.

The programmer/analyzer 40 may be used to obtain various types of information from the implantable device 20. That information may include, for example, sensory data used by the implantable device 20 during the delivery of therapy (e.g., the patient's IEGM, cardiac wall motion data, and physical activity data) and operational parameters of the implantable device 20 (e.g., battery voltage, battery impedance, and lead integrity data). The implantable device 20 also may transmit information relating to the status of internal programmable parameters or data relating to the occurrence of physiological events and the responses of the implantable device 20 to those events (e.g., "marker data"). The ability to examine such data affords the physician the opportunity to fine tune the operation of the implantable device 20 to meet the patient's changing physiological requirements. Further, such data may be collected and stored over an extended period of time, so that the physician can evaluate trends in the performance of the device 20 as well as trends in the patient's condition. A system having such capability is described in commonly-assigned, copending U.S. Pat. application Ser. No. 08/510,369, filed concurrently herewith, of Snell, entitled "A SYSTEM AND METHOD FOR STORING AND DISPLAYING HISTORICAL MEDICAL DATA MEASURED BY AN IMPLANTABLE MEDICAL DEVICE."

The programmer/analyzer 40 may display to the physician the data received from the implanted device 20 in many ways. For example, the programmer/analyzer 40 may provide the physician with the hardcopy printout 80 of the transmitted data in the form of a data listing. Alternatively, a graphical representation (not shown) of the data could be presented on the hardcopy printout 80 or on the display monitor 70.

After reviewing the information received from the implantable device 20, the physician can use the programmer/analyzer 40 to reprogram the implantable device 20, if the data indicates that reprogramming is desirable.

As shown in FIG. 1, the telemetry head 50 is typically secured to the patient 30. However, securing the telemetry head 50 to the patient 30 limits the patient's mobility because the patient 30 is tethered by the communication cable 60 to the programmer/analyzer 40. The cable 60 restricts the distance the patient 30 can move away from the programmer/analyzer 40, and even within that distance, the cable 60 may encumber activities of the patient's 30 by physically interfering with those activities.

Figure 2:
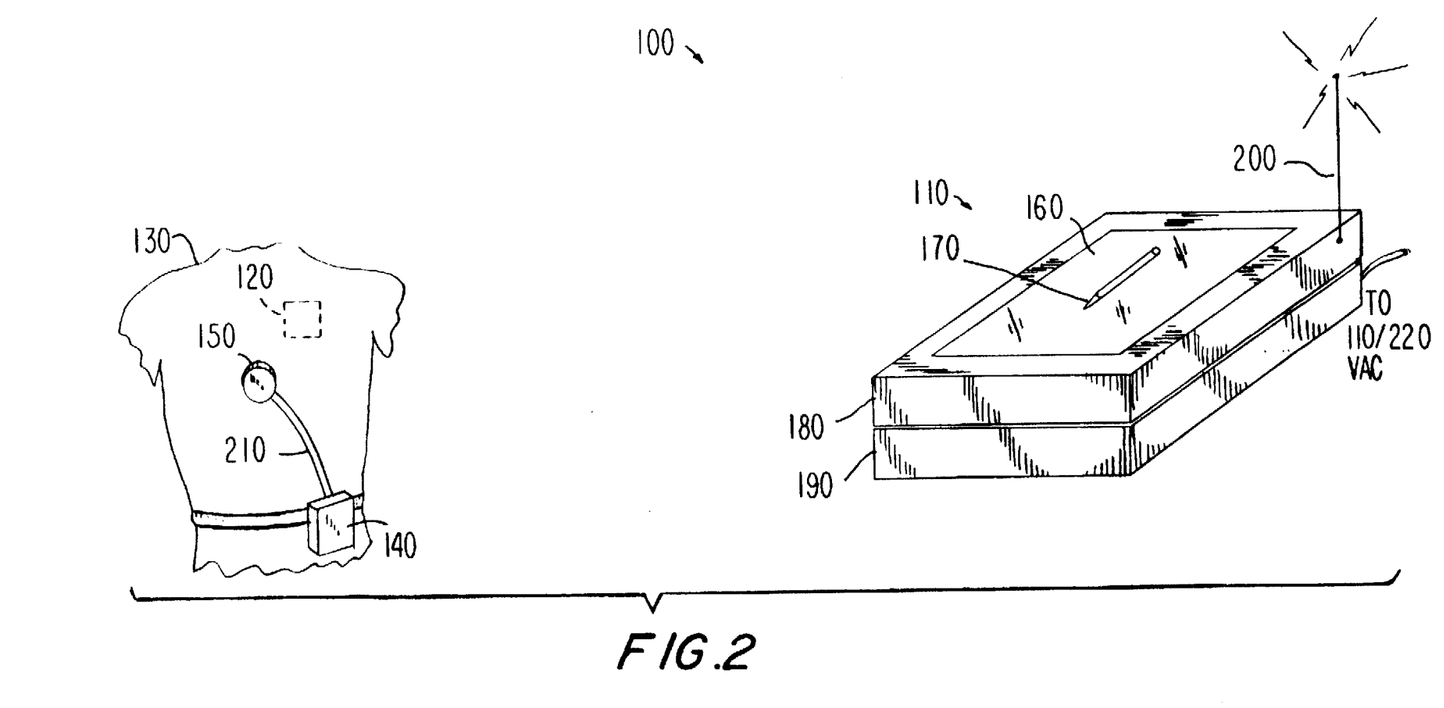
FIG. 2 depicts a tablet computer-based programmer/analyzer which communicates with an implantable medical device using an ambulatory interface unit in accordance with the principles of the present invention.

FIG. 2 shows an ambulatory monitoring and programming system 100 that preferably includes a programmer/analyzer 110, a medical device 120 implanted in a patient 130, and an ambulatory interface unit 140 in accordance with the principles of the present invention. The ambulatory interface unit 140 uses a telemetry head 150 to communicate with the implantable device 120, as discussed in more detail below in connection with FIG. 3.

The programmer/analyzer 110 is preferably a tablet computer-based programmer/analyzer as described in the above-incorporated U.S. patent application entitled "IMPROVED USER INTERFACE FOR AN IMPLANTABLE MEDICAL DEVICE USING AN INTEGRATED DIGITIZER DISPLAY SCREEN." The programmer/analyzer 110 preferably includes a screen 160 that is both a display screen and a digitizing input device. The screen 160 is used by a physician to both view the received data and input data or instructions. The physician may choose, for example, to request data to be transmitted by the implantable device 120 or the physician may choose to input new operational parameters for the implantable device 120. The data supplied by the physician may be entered using a pen-type input device 170 in connection with the screen 160.

The input device 170 and screen 160 may also be used by the physician to manipulate data transmitted by the device 120.

The programmer/analyzer 110 preferably includes a tablet computer 180 and a base station 190. The tablet computer 180 contains a battery (not shown) so that the tablet computer 180 can be removed from the base station 190 when desired. A user enters commands for controlling the programmer/analyzer 110 using the input device 170 and the digitizing screen 160 is used for capturing the movements of the input device 170. However, the input device 170 may also be any other convenient user interface such as a keyboard, light pen, mouse, or trackball (not shown). The display screen 160 is preferably a liquid crystal display screen. By manipulating the input device 170, the user can cause the programmer/analyzer 110 to display physiological data, such as the patient's IEGM, on the display screen 160.

In the preferred embodiment, the programmer/analyzer 110 employs radio-frequency ("RF") communications to transmit data to and receive data from the ambulatory interface unit 140 via an antenna 200. The ambulatory interface unit 140 may be connected to the telemetry head 150 by a communication cable 210. Alternatively, the telemetry head 150 may be incorporated into the ambulatory interface unit 140. The ambulatory interface unit 140 employs conventional telemetry to transmit data to and receive data from the implanted device 120.

Figure 3:
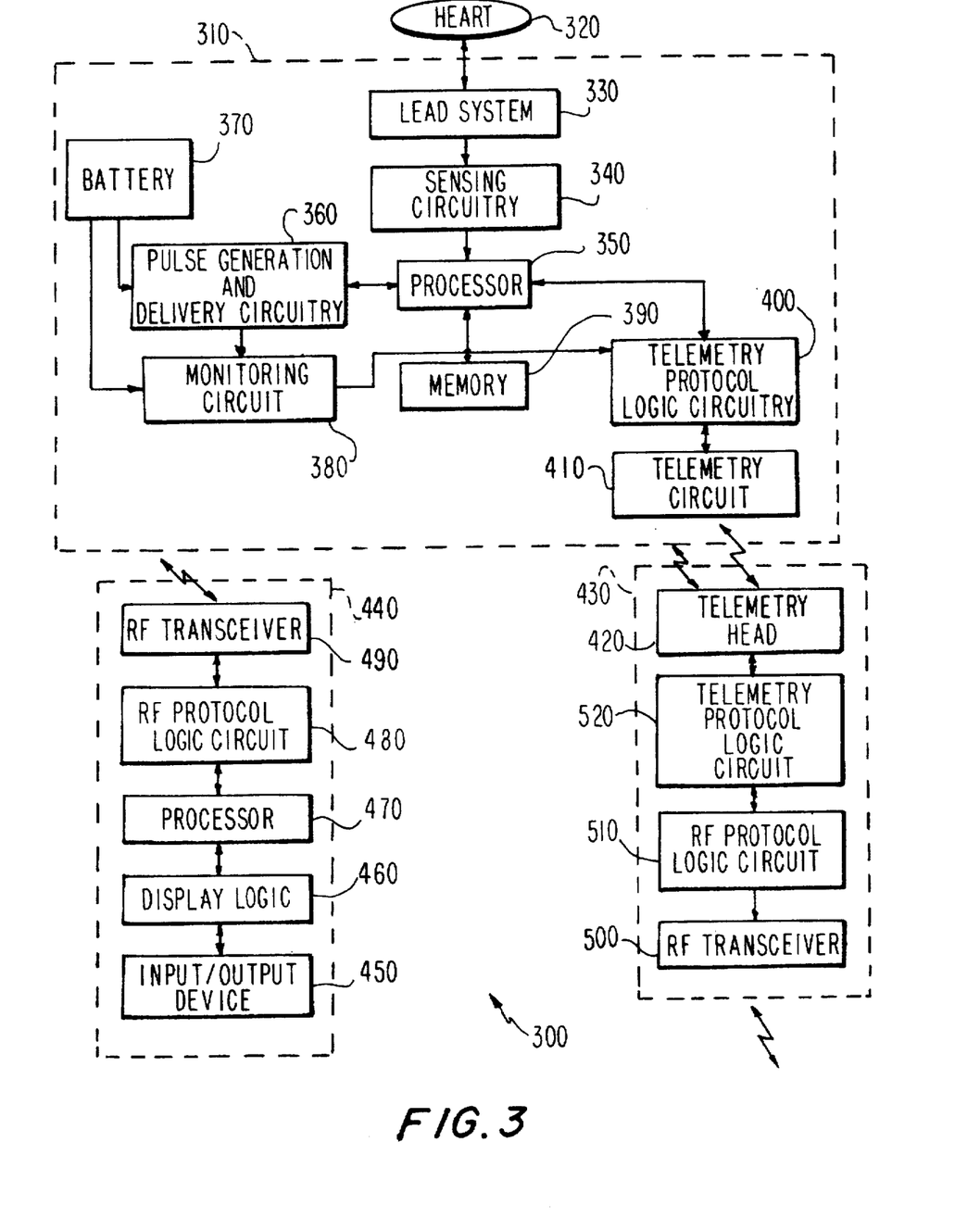
FIG. 3 is a block diagram rendering of a preferred ambulatory monitoring and programming system which includes an ambulatory interface unit in accordance with the principles of the present invention.

Referring now to FIG. 3, a system 300 for communicating with an implantable device 310 which provides, for example, electrical stimulation to a patient's heart 320 is described. The implantable device 310 applies stimulation to the patient's heart 320 through a lead system 330. The lead system 330 also senses cardiac activity in the form of electrical signals (not shown). The electrical signals are transmitted to a sensing circuit 340 that amplifies and digitizes the received analog signals for subsequent use by a processor 350.

The processor 350 performs all of the logic operations required to analyze the digitized signals in order to detect the occurrence of an arrhythmia, classify the type of arrhythmia occurring, and to administer the appropriate therapy. After an arrhythmia is detected and classified, the processor 350 informs a pulse generation and delivery circuit 360 to begin generating a charge of sufficient energy to effectuate the therapy prescribed by the processor 350. A battery 370 supplies power to the pulse generation and delivery circuit 360 as well the entire implantable device 310.

A monitoring circuit 380, such as described in commonly-assigned, copending U.S. patent application Ser. No. 08/227, 838, filed Apr. 14, 1994, of Morgan and Mann, entitled "SYSTEM AND METHOD FOR MEASURING AND STORING PARAMETRIC DATA PERTAINING TO OPERATING CHARACTERISTICS OF AN IMPLANTABLE MEDICAL DEVICE," monitors the operation of the implantable device 310. The monitoring circuit 380 stores in a memory 390 data indicative of the performance of the implantable device 310 including, for example, battery voltage, battery current, and lead system impedance.

The implantable cardiac stimulating device 310 includes a telemetry protocol logic circuit 400 which communicates with the monitoring circuit 380, the processor 350, and the memory 390. The telemetry protocol logic circuit 400 formats the data it receives for telemetric transmission by converting the digital data into a serial bit stream (not shown). The telemetry protocol logic circuit 400 then sends the bit stream to a telemetry circuit 410 which uses the serial bit stream to modulate a signal in a conventional manner.

The modulated signal is transmitted by the telemetry circuit 410 and received by an external telemetry head 420 of an ambulatory interface unit 430 in accordance with the principles of the present invention.

Two-way communication with the implantable device 310 is typically initiated by a physician using a programmer/analyzer 440, such as the tablet programmer/analyzer 110 (FIG. 2), from which instructions or data can be sent to or received from the implantable device 310. For example, the physician, using an input/output device 450 (such as the screen 160 of FIG. 2) can enter a command that instructs the implantable device 310 to transmit physiological data. The transmitted data may have been stored data in the memory 390 or may be transmitted in real time (e.g., transmitted as soon as it is received).

The physician's input is sent to a display logic circuit 460 which digitizes the physician's input and sends it to a processor 470. The processor 470 analyzes the physician's input and produces a digital signal representative of the physician's instruction. It should be noted that while the present example is couched in terms of transmitting an instruction to the implantable device 310, other forms of data could be sent in the same manner. The data could be an addition or a change to data already in the implantable device 310.

In the preferred embodiment, the digital instruction is sent to a radio frequency ("RF") protocol logic circuit 480 which formats the digital instruction into a serial data bit stream which it then uses to modulate a carrier signal. Amplitude or frequency modulation may be used as a matter of design choice. The modulated signal is then transmitted to an RF transceiver 490 for wireless transmission.

An RF transceiver 500 of the ambulatory interface unit 430 receives the modulated signal and sends it to an RF protocol logic circuit 510 which demodulates the signal and extracts the serial data bit stream. Additionally, the RF protocol logic circuit 510 provides for data error checking and correction in a conventional manner such as, for example, a parity bit check with data re-transmission being initiated when an error is detected. Assuming no error has been detected, the RF protocol logic circuit 510 sends the data bit stream to a telemetry protocol logic circuit 520 which formats the data bit stream in a manner suitable for telemetric transmission. The formatted data is then relayed to the telemetry head 420 of the ambulatory interface unit 430 which is placed near the telemetry circuit 410 of the implantable device 310 as described above in connection with FIG. 2.

The telemetry circuit 410 of the implantable device 310 receives the telemetric signal and sends it to the telemetry protocol logic circuit 400. The telemetry protocol logic circuit 400 demodulates the signal, extracts the serial data bit stream, and formats the data bit stream in a manner suitable for use with the processor 350 of the implantable device 310. Additionally, the telemetry protocol logic circuit 400 provides for data error checking and correction in a conventional manner such as, for example, a parity bit check. Assuming no error has been detected, the telemetry protocol logic circuit 400 sends the formatted data to the processor 350 which then begins to execute the instruction.

The implantable device 310 responds to the instruction to transmit data in the following manner. The telemetry protocol logic circuit 400 receives the data from the processor 350, the monitoring circuit 380, or the memory 390 and uses it to modulate a signal for telemetric transmission. The telemetry circuit 410 transmits the modulated signal to the telemetry head 420 of the ambulatory interface unit 430.

The telemetry head 420 of the ambulatory interface unit 430 receives the modulated signal and relays it to the telemetry protocol logic circuit 520. The telemetry protocol logic circuit 520 demodulates the signal and extracts the serial bit stream data. Additionally, the telemetry protocol logic circuit 520 provides for data error detection and correction in a known manner (i.e., parity bit checking resulting in a request for the retransmission of the data when an error is detected).

Assuming no error is detected, in the preferred embodiment, the telemetry protocol logic circuit 520 sends the data to the RF protocol logic circuit 510 which formats the data for radio transmission by modulating a carrier signal with the data. The modulated signal is then sent to the RF transceiver 500 for transmission to the programmer/analyzer 440.

As stated, the programmer/analyzer 440 is preferably a tablet computer-based programmer/analyzer as described above with respect to FIG. 2. However, the present invention may be practiced with any conventional programmer/analyzer that is modified in accordance with the invention. The RF transceiver 490 of the programmer/analyzer 440 receives the modulated signal from the RF transceiver 500. The transceiver 490 relays the modulated signal to the RF protocol logic circuit 480 which demodulates the signal and extracts the data. The RF protocol logic circuit 480 also provides for data error detection and correction should an error arise.

The data is sent to the processor 470 for analysis and processing as needed by the programmer/analyzer 440. The processed data may be sent to the display logic circuit 460 which formats the data in a manner required for display. The display logic circuit 460 sends the data to the input/output device 450 for display.

A physician can view the data obtained from the implantable device 310 and if desired, may request other data or reprogram the device with new parameters. The physician's instruction would follow the same data transmission path as the initial instruction to transmit data, as described above.

In the preferred embodiment, the wireless link between the programmer/analyzer 440 and the ambulatory interface unit 430 is mediated by RF transmissions. However, other wireless communication schemes, for example, infrared communication, are also compatible with the invention. More specifically, spread spectrum infrared may be a desirable way to decrease or eliminate interference associated with conventional RF communications. The distance between the patient and the programmer/analyzer 440 is limited only by the distance necessary for effective communication between the ambulatory interface unit RF transceiver 500 and programmer/analyzer RF transceiver 490.

The invention described herein also contemplates a cellular arrangement wherein the patient wearing an ambulatory interface unit 430 may walk through communication cells which transmit received data to a particular monitoring location. For example, a patient whose physiological vital signs are being monitored may be allowed to walk throughout a hospital without interrupting the monitoring. The patient may walk from cell to cell within the hospital without interrupting data transmissions between the monitoring location and the implantable device 210. The patient is thus ambulatory.

Figure 4:
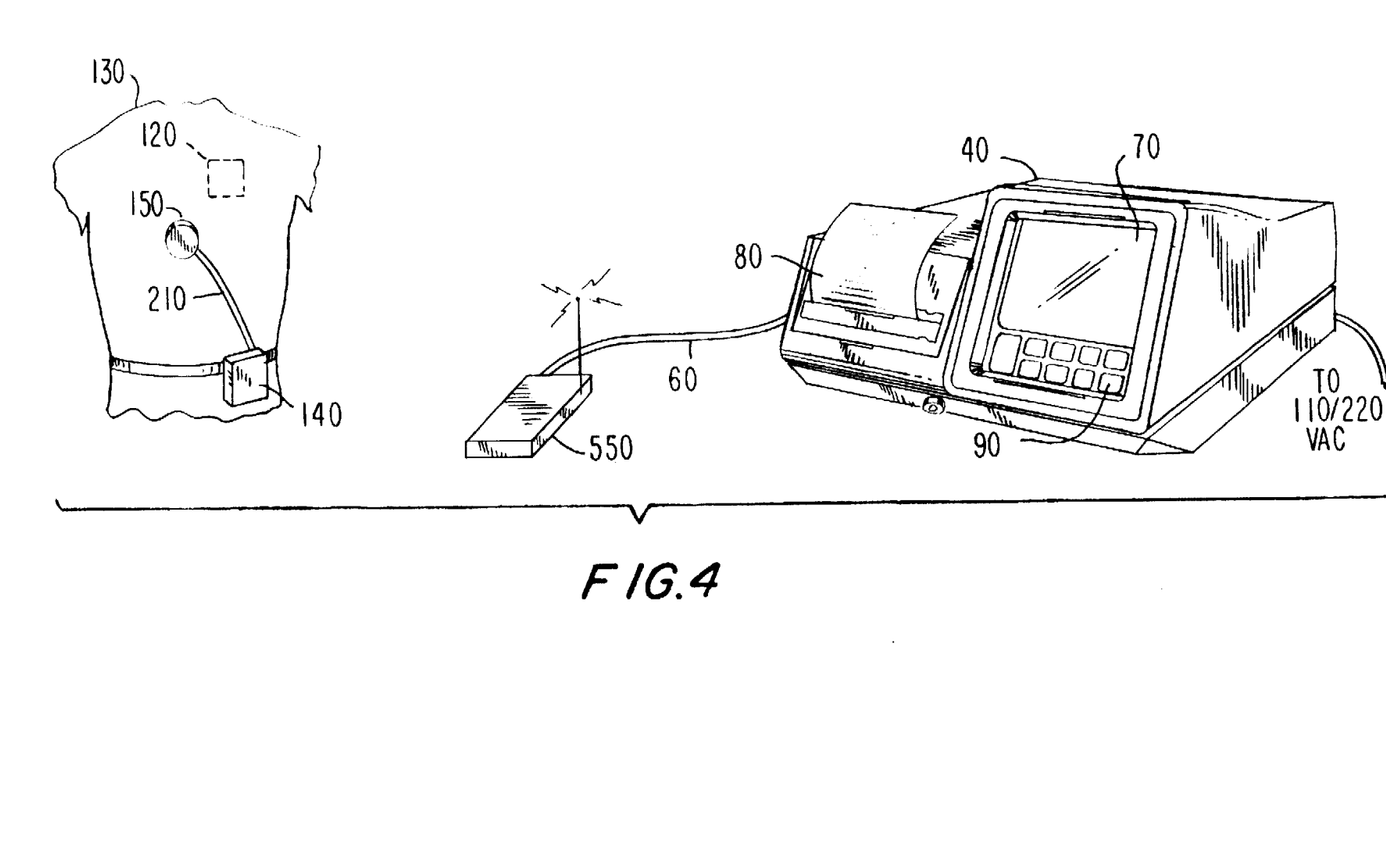
FIG. 4 depicts a conventional programmer/analyzer which is modified to communicate with an implantable medical device in accordance with the principles of the present invention.

The present invention can also be practiced using a conventional programmer/analyzer, as shown in FIG. 4. In FIG. 4, the conventional programmer/analyzer 40 of FIG. 1 is shown coupled to an adapter unit 550 via the communication cable 60. The adapter unit 550 receives telemetry signals from the programmer/analyzer 40 through the communication cable 60. The telemetry signals are converted by the adapter unit 550 to radio frequency signals which are wirelessly transmitted to the ambulatory interface unit 140. The adapter unit 550 also receives radio frequency signals from the ambulatory interface unit 140. The radio frequency signals are converted by the adaptor unit 550 to conventional telemetry signals which are provided to the programmer/analyzer 40 through the communication cable 60.

Thus, a system and method for ambulatory monitoring and programming of an implantable medical device is provided. One skilled in the art will appreciate that the present invention can be practiced by other than the described embodiments, which are presented for purposes of illustration and not of limitation, and the present invention is limited only by the claims that follow.

What is claimed is:

1. An ambulatory medical data communication apparatus comprising:
    an implantable medical device including telemetry means for receiving data transmitted in accordance with a first communication protocol;
    programmer/analyzer means for communicating with the implantable medical device, the programmer/analyzer means including wireless communication means for transmitting data in accordance with a second communication protocol;
    ambulatory interface means for receiving the data transmitted in accordance with the second communication protocol by the wireless communication means of the programmer/analyzer and for transmitting the data in accordance with the first communication protocol to the telemetry means of the implantable medical device; and
    means for securing the ambulatory interface means to a patient.

2. The apparatus of claim 1, wherein:
    the telemetry means transmits data from the implantable medical device in accordance with the first communication protocol;
    the wireless communication means of the programmer/analyzer means receives data transmitted in accordance with the second communication protocol; and
    the ambulatory interface means receives the data transmitted in accordance with the first communication protocol by the telemetry means and transmits the data received from the telemetry means to the wireless communication means of the programmer/analyzer means in accordance with the second communication protocol.

3. The apparatus of claim 2, wherein the data transmitted by the programmer/analyzer means comprises an instruction to the implantable medical device to transmit data.

4. The apparatus of claim 1, wherein:
    the wireless communication means of the programmer/analyzer means comprises radio frequency transmitting means for transmitting radio frequency modulated carrier signals representing the data transmitted by the programmer/analyzer means; and
    the ambulatory interface means comprises:
        radio frequency receiving means for receiving the modulated carrier signals;
        radio frequency protocol logic means for demodulating the modulated carrier signals to extract the data transmitted by the programmer/analyzer means;
        telemetry protocol logic means for formatting the data transmitted by the programmer/analyzer means for telemetric transmission; and
        a telemetry head for telemetrically transmitting the formatted data to the telemetry means of the implantable medical device.

5. The apparatus of claim 4, wherein the radio frequency protocol logic means detects errors in the data transmitted by the programmer/analyzer means.

6. The apparatus of claim 4, wherein the radio frequency transmitting means uses amplitude modulation.

7. The apparatus of claim 4, wherein the radio frequency transmitting means uses frequency modulation.

8. The apparatus of claim 1, wherein the programmer/analyzer means comprises a tablet computer-based programmer/analyzer.

9. The apparatus of claim 1, wherein the implantable medical device comprises an implantable cardiac stimulating device.

10. The apparatus of claim 1, wherein the data transmitted by the programmer/analyzer means comprises operating instructions for the implantable medical device.

11. The apparatus of claim 1, wherein the programmer/analyzer means comprises adapter means, the wireless communication means being disposed within the adapter means.

12. An ambulatory medical data communication apparatus comprising:
    a medical device implantable in a patient, the implantable medical device including telemetry means for transmitting telemetry signals representing data in accordance with a first communication protocol;
    programmer/analyzer means for communicating with the implantable medical device, the programmer/analyzer including wireless communication means for receiving data in accordance with a second communication protocol, the programmer/analyzer being adapted to monitor the performance of the implantable medical device in response to the received data;
    ambulatory interface means for receiving the telemetry signals transmitted in accordance with the first communication protocol and for transmitting data represented by the telemetry signals to the wireless communication means of the programmer/analyzer means in accordance with the second communication protocol; and
    means for securing the ambulatory interface means to a patient, the performance of the implantable medical device being monitorable by the programmer/analyzer while the patient is ambulatory.

13. The apparatus of claim 12, wherein:
    the wireless communication means of the programmer/analyzer means comprises radio frequency receiving means for receiving radio frequency modulated carrier signals; and
    the ambulatory interface means comprises:
        a telemetry head for receiving the telemetry signals from the telemetry means of the implantable medical device;
        telemetry protocol logic means for extracting the data from the telemetry signals;
        radio frequency protocol logic means for generating radio frequency modulated signals representing the data; and
        radio frequency transmitting means for transmitting the modulated carrier signals to the radio frequency receiving means of the programmer/analyzer means.

14. The apparatus of claim 13, wherein the telemetry protocol logic means detects errors in the data transmitted by the telemetry means of the implantable medical device.

15. The apparatus of claim 13, wherein the radio frequency transmitting means uses amplitude modulation.

16. The apparatus of claim 13, wherein the radio frequency transmitting means uses frequency modulation.

17. The apparatus of claim 12, wherein the programmer/analyzer means comprises a tablet computer-based programmer/analyzer.

18. The apparatus of claim 12, wherein the implantable medical device comprises an implantable cardiac stimulating device.

19. The apparatus of claim 12, wherein the programmer/analyzer means comprises adapter means, the wireless communication means being disposed within the adapter means.

20. A method of wirelessly communicating data between a programmer/analyzer and an implantable medical device, comprising the steps of:
   transmitting data in accordance with a first communication protocol from the programmer/analyzer using wireless communication circuitry of the programmer/analyzer;
   receiving the data transmitted in accordance with the first communication protocol by the wireless communication circuitry of the programmer/analyzer using an ambulatory interface unit;
   securing the ambulatory interface unit to a patient; and
   transmitting the data in accordance with a second communication protocol from the ambulatory interface unit to telemetry circuitry of the implantable medical device.

21. The method of claim 20, further comprising the steps of:
   transmitting data in accordance with the second communication protocol from the implantable medical device using the telemetry circuitry;
   receiving the data transmitted in accordance with the second communication protocol by the telemetry circuitry using an ambulatory interface unit; and
   transmitting the data in accordance with the first communication protocol from the ambulatory interface unit to the wireless communication circuitry of the programmer/analyzer.

22. The method of claim 21, wherein the step of transmitting data from the programmer/analyzer comprises transmitting an instruction to the implantable medical device to transmit data.

23. The method of claim 20, further comprising the step of detecting errors in the data transmitted by the programmer/analyzer.

24. The method of claim 20, wherein the data is transmitted from the programmer/analyzer using amplitude modulated radio frequency signals.

25. The method of claim 20, wherein the data is transmitted from the programmer/analyzer using frequency modulated radio frequency signals.

26. The method of claim 20, wherein the step of transmitting data from the programmer/analyzer comprises transmitting the data from a tablet computer-based programmer/analyzer.

27. The method of claim 20, wherein the step of transmitting data to the implantable medical device comprises transmitting data to an implantable cardiac stimulating device.

28. A method of wirelessly communicating data between a programmer/analyzer and a medical device implantable in a patient, the programmer/analyzer being adapted to monitor the performance of the implantable medical device, the method comprising the steps of:
   transmitting data in accordance with a first communication protocol using telemetry circuitry of the implantable medical device;
   receiving the data transmitted in accordance with the first communication protocol by telemetry circuitry of the implantable medical device using an ambulatory interface unit;
   securing the ambulatory interface unit to a patient; and
   transmitting the data in accordance with a second communication protocol from the ambulatory interface unit to wireless communication circuitry of the programmer/analyzer, the performance of the implantable medical device being monitorable by the programmer/analyzer in response to the data while the patient is ambulatory.

29. The method of claim 28, further comprising the step of detecting errors in the data transmitted by the implantable medical device.

30. The method of claim 28, wherein the data is transmitted from the ambulatory interface unit using amplitude modulated radio frequency signals.

31. The method of claim 28, wherein the data is transmitted from the ambulatory interface unit using frequency modulated radio frequency signals.

32. The method of claim 28, wherein the step of transmitting data from the ambulatory interface unit comprises transmitting the data from the ambulatory interface unit to a tablet computer-based programmer/analyzer.

33. The method of claim 28, wherein the step of transmitting data from the implantable medical device comprises transmitting data from an implantable cardiac stimulating device.

34. An ambulatory medical data communication apparatus comprising:
   an implantable medical device including telemetry means for receiving data transmitted in accordance with a first communication protocol;
   programmer/analyzer means for communicating with the implantable medical device, the programmer/analyzer means including wireless communication means for transmitting data in accordance with a second communication protocol, wherein the programmer/analyzer means comprises a tablet computer-based programmer/analyzer; and
   ambulatory interface means for receiving the data transmitted in accordance with the second communication protocol by the wireless communication means of the programmer/analyzer and for transmitting the data in accordance with the first communication protocol to the telemetry means of the implantable medical device.

35. An ambulatory medical data communication apparatus comprising:
   an implantable medical device including telemetry means for transmitting telemetry signals representing data in accordance with a first communication protocol;
   programmer/analyzer means for communicating with the implantable medical device, the programmer/analyzer including wireless communication means for receiving data in accordance with a second communication protocol, wherein the programmer/analyzer means comprises a tablet computer-based programmer/analyzer; and
   ambulatory interface means for receiving the telemetry signals transmitted in accordance with the first communication protocol and for transmitting data represented by the telemetry signals to the wireless communication means of the programmer/analyzer means in accordance with the second communication protocol.

36. A method of wirelessly communicating data between a tablet programmer/analyzer and an implantable medical device, comprising the steps of:

transmitting data in accordance with a first communication protocol from the tablet programmer/analyzer using wireless communication circuitry of the tablet programmer/analyzer;

receiving the data transmitted in accordance with the first communication protocol by the wireless communication circuitry of the tablet programmer/analyzer using an ambulatory interface unit; and transmitting the data in accordance with a second communication protocol from the ambulatory interface unit to telemetry circuitry of the implantable medical device.

37. A method of wirelessly communicating data between a tablet programmer/analyzer and an implantable medical device, comprising the steps of:

transmitting data in accordance with a first communication protocol using telemetry circuitry of the implantable medical device;

receiving the data transmitted in accordance with the first communication protocol by telemetry circuitry of the implantable medical device using an ambulatory interface unit; and transmitting the data in accordance with a second communication protocol from the ambulatory interface unit to wireless communication circuitry of the tablet programmer/analyzer.

* * * * *